United States Patent [19]

Iudica

[11] 4,231,739
[45] Nov. 4, 1980

[54] UNITARY CARTRIDGE TYPE TURBINE ASSEMBLY

[75] Inventor: Robert T. Iudica, N. Babylon, N.Y.

[73] Assignee: Professional Mfg. Corp., Deer Park, N.Y.

[21] Appl. No.: 29,710

[22] Filed: Apr. 11, 1979

[51] Int. Cl.³ .................................................. A61C 1/08
[52] U.S. Cl. ...................................... 433/126; 433/132
[58] Field of Search ................. 415/503; 433/132, 126

[56] References Cited

U.S. PATENT DOCUMENTS

| | | | |
|---|---|---|---|
| 3,268,205 | 8/1966 | Allen et al. | 433/132 |
| 4,071,954 | 2/1978 | Eibofner | 433/132 |

*Primary Examiner*—Robert Peshock
*Attorney, Agent, or Firm*—Bauer & Amer

[57] ABSTRACT

A unitary turbine assembly in the form of a cartridge readily inserted as a unit in turbine operated dental handpieces and removable as a unit therefrom for replacement without damage to or requiring change or modification of the housing of the handpiece in which the turbine assembly is contained.

15 Claims, 6 Drawing Figures

UNITARY CARTRIDGE TYPE TURBINE ASSEMBLY

BACKGROUND OF THE INVENTION

This invention relates to dental handpieces. More particularly, it relates to a unitary turbine assembly that is usable in the form of a cartridge to be interchangeable in dental handpieces of different manufactures by simple and ready insertion into the housing of the turbine operated dental handpiece and removal therefrom when replacement is required.

The advent of turbine operated dental handpieces has spawned a variety of turbine constructions. Each manufacturer has sought to innovate their own turbine structures such that there is little likelihood that any two such handpieces are interchangeable with each other. As a result, each manufacturer has a virtual monopoly on the sale of replacement parts and specialized tools for the repair of such handpieces, no less in the actual repair of the same.

Whether each manufacturer deliberately manufactures his products with special attention to assure for himself a monopoly of the replacement and repair after market is unimportant in the consideration of the present invention. What is important is that in the absence of uniformity and standardization practices amongst manufacturers of dental handpieces, the cost of replacement parts and their repair becomes expensive and time consuming.

Simple examples of non-standardized dental handpieces of the prior art are found in U.S. Pat. Nos. 2,945,299 and 3,324,553. In each such example there is included an arrangement of turbine structure for the operation of a dental tool or burr. In such exemplary handpieces great care and specialized tools must be employed to assure the smooth and aligned relationship between the parts of the turbine assembly and the head of the handpiece. Any misalignment between the two will result in improper operation of the turbine and will cause the rapid deterioration of its related parts along with possible damage to the head in which the turbine is mounted within the handpiece.

In like manner, when it is necessary to replace any one of the worn or damaged turbine parts, they must be carefully removed from the head of the headpiece. If the head is scratched or scarred or abraded in any manner, it will need to be rebored, or repaired, or thrown away. Thus, in order to properly remove a worn turbine assembly of parts and effectively replace the same with a new set of turbine parts, specialized tools and skills are required to overcome the problems inherent in the disassembly and assembly of the same and to prevent damage either to the handpiece and/or to the parts of the turbine assembly.

An object of the invention is to provide a unitary turbine cartridge type assembly that may be used interchangeably with many differently configured and sized heads of dental handpieces, either as original equipment therewith or as replacement parts therefor. The present invention is directed toward the solution of the aforementioned problems by providing an essentially standard unitized turbine assembly for use in a dental handpiece. The inventive unitized turbine assembly is so simple in construction and relatively inexpensive to manufacture that it is self-contained and requires no special tools for its insertion into or removal from the head or housing of a dental handpiece and requires no special skills to insert or remove from the dental handpiece.

The desideratum of the invention is to provide a unitary turbine assembly that is preassembled as a complete cartridge type structure to enable it to be readily substituted as a replacement unit or cartridge for a worn turbine assembly of parts in a fluid operated dental handpiece which has an interior housing of generally circular configuration.

Another object and feature of the invention is to provide a unitary turbine assembly that obviates the need for its own housing, but cooperates with and utilizes the interior wall of the housing or head of the dental handpiece as its own housing to entrap the pressurized fluid, as air, to drive the turbine.

In this connection, still a further object and feature of the invention is the bearing support of yieldable sealing structures that conformingly engage with the wall of the housing of the handpiece to confine and direct the driving fluid against the blades of the impeller of the turbine.

The above description, as well as further objects, features and advantages of the present invention, will be more fully appreciated by reference to the following detailed description of a presently preferred, but nonetheless illustrative, embodiment in accordance with the present invention when taken in conjunction with the accompanying drawings wherein.

Figure 2:
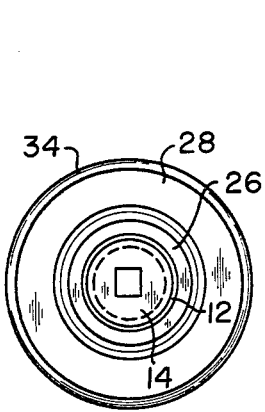
FIG. 2 is a left side view of FIG. 1.
Figure 1:
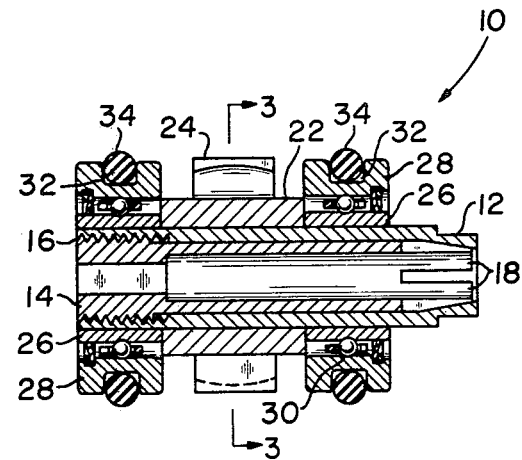
FIG. 1 is a cross-sectional view of a unitary turbine assembly constructed according to the invention.
Figure 3:
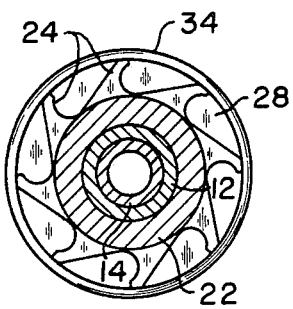
FIG. 3 is a cross-section taken on line 3—3 of FIG. 1.
Figure 4:
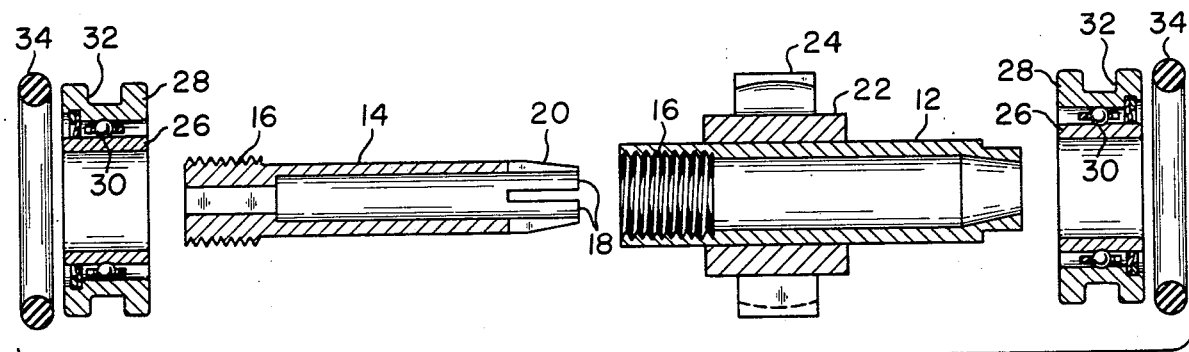
FIG. 4 is an expanded view of the unitary turbine assembly shown in FIG. 4.

Referring now to the drawing, the unitary turbine assembly is generally identified by the numeral 10. The assembly 10 includes a sleeve-shaped structure of an axially directed hollow spindle 12 that is connected with an interior supported chuck 14. They are releasably and jointly rotatable at a threaded connection 16 formed on the interior of the spindle and on the exterior of the chuck.

The chuck 14 is provided with a plurality of spring fingers 18 that are operated radially to releasably engage with and rotate a dental tool (not shown) as a burr or the like when the spindle and chuck move axially relative to each other along their threaded engagement 16. As is common in such turbine assemblies, the chuck is provided about the outer periphery of the chuck fingers 18 with a tapered surface 20. The cooperating inner surface of the spindle 12 is similarly tapered such that upon relative rotation and axial movement of the spindle and chuck, the fingers 18 are selectively actuated to move relative to each other radially to close and grip the shaft of a dental tool positioned therebetween or to release the same.

Mounted intermediate the ends of the sleeve 12 for rotation therewith and from longitudinal movement relative thereto is a body 22 of an impeller or turbine.

The axial body 22 is provided with a plurality of curved turbine or impeller blades 24 that project substantially radially outward from the body 22. For the purpose of the present invention, let it suffice to note that the blades 24 may be of any conventional design employed in turbines of dental handpieces.

Relatively spaced from each other and at opposite ends of the turbine body 22 and in limited abutment therewith are two rollable bearings each having an inner race 26 and an outer race 28 and rolling elements 30 therebetween. The inner races 26 abut against the opposite ends of the turbine body 22 to restrict the accidental displacement thereof relative to the sleeve and are also similarly affixed to the sleeve 12 so that they rotate jointly therewith. By this same positioning of the inner bearing races 26 and turbine body 22 in rotative connection with the sleeve 12, that is also connected with the chuck 14, the whole of these elements are combined to form a unitized turbine assembly that is easily utilized and manipulated as a single cartridge type structure.

The outer races 28 are constructed about their outer peripheral surfaces with a U-shaped indented seat 32. Each seat is purposely formed as a U-shape to positively receive therein a single circumferentially disposed shaped sealing engaging element 34. The elements 34 are of singular construction so as to assure that the outer peripheral surface thereof is capable of making complete circumferential engagement with a mating surface to form a fluid-tight sealing engagement therewith in a manner to be described.

Each of the elements 34 is made of a material, as solid rubber, that is relatively yieldable in response to forces applied thereto and thus therefore expandable and also deformable to an extent as to conform itself into the tight-fitting engagement with the wall with which it comes into contact while having inherent resilience to flex, cushion and absorb forces applied to it when it is engaged between the assembly 10 and the dental handpiece housing with which it is to cooperate. By reason of its positive positioning within the circumferential seat 32, the engaging means 34 becomes an integral part of the unitary assembly 10 and is dislodged therefrom by prying the same free of the seat. Otherwise, the element 34 is in actual fact a physical unitary part of the assembly 10.

The unitized turbine assembly 10 as aforedescribed is unlike any prior known dental turbine structure in that it is in the form of a cartridge that is open about its exterior. That is to say, the assembly 10 is constructed without any bounding or confining exterior wall. This means that the sealing-engaging means 34 is initially unconfined and free of engagement with any structure other than the seat 32 in which it is positively retained.

Those skilled in the art will recognize the uniqueness of this wall-less or unconfined arrangement because it enables the elements 34 to function as the logical force absorbing sealing engagement between the assembly 10 and the interior wall of the many differently configured turbine housings of dental handpieces with which the same will be utilized. Where, in the past, the worn or damaged turbine assembly could only be replaced by one of the same manufacturer, it is now possible to enable substitution of the present turbine assembly 10 and thereby release users from the restriction of having to deal only with the handpiece manufacturer.

Furthermore, because of the wall-less construction of the present inventive teaching, it is now possible to utilize a turbine assembly 10 even with a scarred wall of a dental handpiece. In the past whenever the interior wall of the turbine housing was scarred or otherwise damaged, it was necessary to repair it before inserting into it a walled turbine assembly. If repairs were not feasible because of cost or other reasons, the costly handpiece was discarded. By the present inventive teaching, the elements 34 take advantage of the presence of the already existing wall of the handpiece housing and utilizes the same to cooperate therewith by engaging against it and forming a seal with it to, in effect, cause the wall of the housing of the handpiece to become the actual wall of the wall-less inventive unitary turbine assembly 10.

Figure 5:
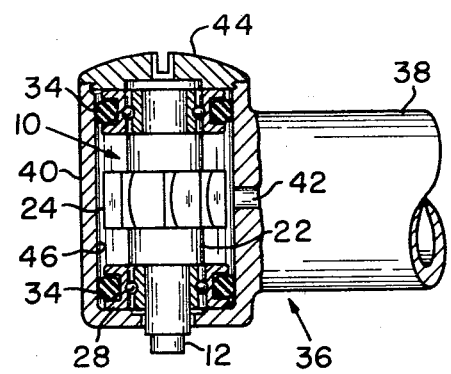
FIG. 5 is a vertical cross-sectional view of the head and a portion of the handle of a dental handpiece with the unitary cartridge type turbine assembly contained therein according to the invention.

Attention is directed to FIG. 5 wherein there is generally illustrated an exemplary handpiece generally identified by the numeral 36 that has a handle 38 formed with a turbine housing 40. The handpiece 36 forms no part of the present invention but those familiar therewith will know that it includes air passages to direct air from a pressure source to the turbine to operate the turbine therein and an air outlet means from the housing 40 after the air has performed its function on the turbine blades. In FIG. 5 the opening 42 in the housing 40 is a graphic illustration of the air inlet under pressure into the housing and of the air exhaust from the housing. The housing 40 is often closed by a threaded screw 44 as illustrated in FIG. 5.

When it is desired to replace or substitute a worn turbine assembly with the inventive assembly 10, the covering cap screw 44 is removed and the old turbine parts are forced outward therefrom from engagement with the interior wall 46 thereof. The present unitized assembly 10 is then manipulated as a single cartridge and slid into the housing 40. No special tools or fixtures are required for this purpose. In practice it has been found that the insertion of the assembly 10 is handled as a single cartridge and easily accomplished simply by first lubricating the wall 46 and the engaging elements 34. This enhances their relative frictionless sliding movement.

After the tool engaging sleeve 12 and chuck 14 are pushed fully into the housing 40 to extend therebeyond as shown in FIG. 5, the whole assembly 10 may be backed out slightly and then pushed back in again fully. This relative back and forth sliding movement will help the bearings to align themselves properly and to assure the proper seating of the engaging elements 34 in their respective seats 32. It will also assure a good fluid-tight seal and surface engagement between the elements 34 and the wall 46 and a flattening of the engaging periphery of the elements 34 with the wall 46 so as to provide for an area or surface sealing contact and engagement therebetween.

When so mounted within the housing 40, the assembly 10 now adopts and utilizes the wall 46 as its own by virtue of the engagement between the elements 34 therewith. This cooperation encloses the turbine so that the air inlet-exhaust 42 is essentially entrapped between the seals 34. Air emanating from the inlet 42 into the housing 40 impinges upon the turbine blades 24 and is confined within the space between the engaging seals 34 until it has had the opportunity to be fully utilized. It is then permitted to exhaust from the chamber defined between the elements 34 and the wall 46 and out of the housing 40 through the air outlet (42) that is commonly provided in such dental handpieces as previously described herein.

The present turbine assembly 10 has been found to be unusually efficient, with the turbine itself operating at no load in excess of 300,000 r.p.m. The engaging seal means 34 mounted on opposite sides of the turbine, being sufficiently resilient, have an inherent cushioning capability that provide a cushioning effect between the outer race of each of the bearings and the wall 46. This permits the elements 34 to absorb vibrating forces between the assembly 10 and the housing 40.

The air gap or spillway between the impeller blades 24 and the bearings on the opposite sides thereof is effectively maintained by the seal between the elements 34 and the wall 46. It has been found that this spillway may be maintained from between 0.030 inches and 0.060 inches without adversely affecting the operation of the turbine. A further air gap of between 0.010 inches and 0.030 inches between the outer diameter of the blades 24 and the adopted wall 46 may be provided without adversely affecting the operating characteristics of the assembly 10 within the housing. The gaps so defined enable the full use of the input air against the blades 24 while affording sufficient space within which the air can escape from between the blades to avoid the deleterious air turbulence that acts against the rear of each turbine blade which tends to slow down the turbine rotation until such time as the air can be exhausted at a point approximately 300° beyond the air input point. The air gaps thus provide a sufficient space that avoids the occurrence of turbulence.

Figure 6:
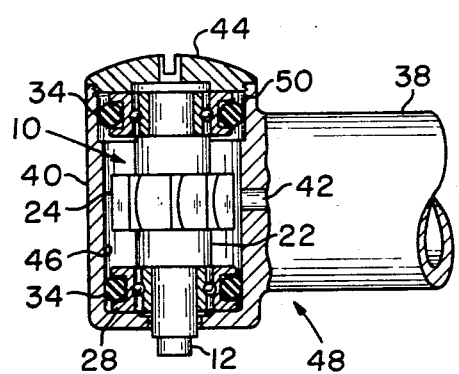
FIG. 6 is a vertical cross-sectional view of the head and a portion of the handle of another dental handpiece showing the use of the unitary cartridge type turbine assembly therewith.

In the exemplary handpiece 36 of FIG. 5, the wall 46 thereof is illustrated as being of uniform diameter throughout its length. This illustration should not be considered a limitation upon the scope of the invention. For example, in FIG. 6 the handpiece 48 thereshown is in all essential respects like that of the handpiece 36 of FIG. 5. For this reason, like parts are like numbered. In FIG. 6 the wall 46 thereof is illustrated as having a stepped or larger diameter 50 to illustrate the versatility of the present invention for use therewith. The inventive assembly 10 is illustrated mounted operatively within the housing 40 of FIG. 6.

Where the housing 40 is of non-uniform diameter as in FIG. 6, the present invention is readily able to be adapted to function therewith. Hence, where the wall 40 is stepped or changed in size as illustrated at 50, the seal engagement means or elements 34 may be similarly varied in size. Accordingly, it is within the teaching of the invention that where the wall 50 is larger in diameter than the integrity of the sealing engagement that a selected element 34 may make with it, another element 34 of different size may be selected. Such other selected element 34 should have the expansive and deformation characteristics that will enable it to effect the resilient cushioning absorption of forces between the housing 40 and the assembly 10 while, at the same time, making the aforedescribed sealing engagement with the stepped surface 50.

While there have been shown and described and pointed out the fundamental novel features of the invention as applied to a preferred embodiment thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

What is claimed is:

1. A self-contained cartridge assembly free of any outer enclosure for insertion and use as a unit in and for removal from a plurality of dental handpieces in which the housing interiors are different in size and in which each housing has a fluid inlet to direct fluid into the housing and an outlet to exhaust fluid from the housing and in which the housing becomes the enclosure for said cartridge assembly when said cartridge assembly is positioned therein, said cartridge assembly comprising
  sleeve shaped means of substantially the length of the housing and for engagement with a dental tool,
  a turbine having impeller faces extending into the housing and for impingement thereagainst by fluid directed into the housing through the fluid inlet thereof to rotate said turbine,
  said impeller being connected with said sleeve for conjoint rotation therewith,
  rollable bearings fixed on said sleeve on opposite sides of said impeller,
  and engaging means captured on said rollable bearings extending outward therefrom for fluid tight engagement with the wall of the handpiece housing on opposite ends of said impeller to confine and direct the inlet fluid against said impeller and the faces thereof to contain the fluid from flowing outward from between said cartridge and the engagement of said engaging means with the housing.

2. In a cartridge type turbine assembly as in claim 1, said engaging means being yieldable to cushion the engagement between said cartridge type turbine assembly and the housing to absorb vibrations therebetween.

3. In a cartridge type turbine assembly as in claim 2, said engaging means being of a size and being deformable to engage fluid tightly with housing walls of different sizes.

4. In a cartridge type turbine assembly as in claim 3, seat means on said rollable bearings mounting said engaging means to support the same in fixed position thereon and to prevent removal of said engaging means from their respective bearing.

5. In a cartridge type turbine assembly as in claim 3, said rollable bearings being spaced from and on opposite sides of said impeller faces from between 0.030 inches to 0.060 inches, and said impeller faces being spaced from the wall of the housing from between 0.010 inches and 0.030 inches.

6. In a cartridge type turbine assembly as in claim 1, said rollable bearings being spaced from and on opposite sides of said impeller faces from between 0.030 inches to 0.060 inches.

7. In a cartridge type turbine assembly as in claim 1, said impeller faces being spaced from the wall of the housing from between 0.010 inches and 0.030 inches.

8. In combination with a turbine operated dental handpiece having a housing with an interior wall to accommodate a turbine and fluid inlet and outlet means for the supply and exhaust respectively of fluid from the housing, a unitary turbine assembly free of any enclosure comprising
  rollable bearings relatively spaced from each other and each said bearing having inner and outer races,
  a rotatable turbine in said space between said bearings and having a plurality of impeller faces to receive the impingement of fluid thereagainst in the housing, seal means captured on the outer races of said bearings in fluid tight direct engagement with the interior wall of the housing to enclose said turbine between said spaced bearings and the interior wall such that fluid entering the housing is caused to impinge upon the impeller faces and to exhaust outward from the housing through the fluid outlet means, and an elongated dental tool holder mounting said bearings in their spaced relationship and with said turbine therebetween, said tool holder including a sleeve connected with said inner races of said bearings and with said turbine to rotate conjointly therewith, and said seal means being releasably engageable with the interior wall of the housing to enable said unitary turbine assembly to be inserted into and removed from engagement as a unit with the housing wall so that the housing becomes the enclosure for the unitary turbine assembly.

9. A unitary turbine assembly as in claim 8,
said seal means being of a yieldable material and engaging with the interior walls of different sizes of housings fluid tightly to cause the outer race of its respective bearing to be non-rotatable relative to such engaged wall.

10. A unitary turbine assembly as in claim 8,
said bearings being spaced from and on opposite sides of said rotatable turbine from between 0.030 inches to 0.060 inches.

11. A unitary turbine assembly as in claim 8,
said impeller faces being spaced from the wall of the housing of the dental handpiece from between 0.010 inches to 0.030 inches.

12. A unitary turbine assembly as in claim 8,
a recessed seat defined in the periphery of each of the outer races of said bearings,
and said seal means on each of the outer races of said bearings being mounted within a respective one of said peripheral seats to retain the seal means fixed with respect to its respective bearing unitl forcefully removed therefrom for replacement.

13. A wall-less unitary cartridge type turbine assembly free of an outer enclosure for use in a circular housing of a dental handpiece in which the interior circular wall of the housing is utilized as the wall of the turbine assembly, said assembly comprising a rotatable axially elongated chuck having operable means for releasable engagement with a dental tool, a sleeve connected with said chuck for rotation therewith and rotation relative thereto to actuate said operable means to releasably engage a dental tool, a turbine on said sleeve intermediate the ends thereof for rotation therewith, said turbine having a plurality of circumferentially spaced impeller faces against which fluid may impinge to rotate said turbine, rollable bearings spaced axially along said sleeve and on opposite sides of said impeller and axially from said impeller faces, each of said rollable bearings having inner and outer races with said inner race connected with said sleeve for rotation therewith and said outer race being rotatable with respect thereto, and seal means of yieldable deformable material mounted on said outer race of each of said bearings and from displacement therefrom so that said chuck, sleeve, turbine, rollable bearings and seal means are connected together as a unit free of an enclosing wall and for use as a cartridge type insert into and for removal from the housings of different dental handpieces with said seal means yielding to fit into the interior wall of the housing and deforming into fluid-tight engagement therewith such that the housing wall becomes the temporary enclosing wall of said turbine assembly while the same is therein and until said turbine assembly is removed from said housing by disengagement of said seal means therefrom.

14. A wall-less unitary cartridge type turbine assembly as in claim 13,
said outer races of each of said rollable bearings having a circumferential seat defined in the outer periphery thereof in which said seal means is mounted and prevented from displacement.

15. A wall-less unitary cartridge type turbine assembly as in claim 13,
said rollable bearings being spaced on opposite axial sides of said impeller faces from between 0.030 inches and 0.060 inches and said impeller faces being arranged on said unitary cartridge type turbine assembly such that when the same is within the housing said impeller faces are spaced from the interior wall thereof from between 0.010 inches and 0.030 inches.

* * * * *